(12) United States Patent
Paton et al.

(10) Patent No.: US 6,536,370 B2
(45) Date of Patent: *Mar. 25, 2003

(54) ELAPSED TIME INDICATOR FOR CONTROLLED ENVIRONMENTS AND METHOD OF USE

(75) Inventors: Eric Paton, Morgan Hill, CA (US); Balaraman Mani, Cupertino, CA (US)

(73) Assignee: Advanced Micro Devices, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/199,349

(22) Filed: Nov. 25, 1998

(65) Prior Publication Data

US 2002/0000184 A1 Jan. 3, 2002

(51) Int. Cl.$^7$ .............................................. G01D 21/00
(52) U.S. Cl. ...................................... 116/206; 374/102
(58) Field of Search ................................ 116/206, 207, 116/216, 219; 368/327; 426/87, 88; 379/102, 104, 106, 107, 108; 206/204

(56) References Cited

U.S. PATENT DOCUMENTS

| | | | | |
|---|---|---|---|---|
| 3,018,611 A | * | 1/1962 | Biritz ......................... 116/206 |
| 3,480,402 A | * | 11/1969 | Jackson ..................... 116/206 |
| 3,898,172 A | * | 8/1975 | Reif et al. ................ 252/408.1 |
| 4,098,120 A | | 7/1978 | Manske |
| 4,201,080 A | * | 5/1980 | Slepak et al. .............. 116/206 |
| 4,408,557 A | * | 10/1983 | Bradley et al. ............. 116/206 |
| 4,550,676 A | * | 11/1985 | Francis ....................... 116/206 |
| 4,789,637 A | * | 12/1988 | Preziosi et al. ............. 116/206 |
| 4,793,180 A | * | 12/1988 | Stewart et al. .............. 116/200 |
| 4,812,053 A | * | 3/1989 | Bhattacharjee .............. 116/206 |
| 4,859,360 A | * | 8/1989 | Suzuki et al. ............... 374/162 |
| 4,909,179 A | * | 3/1990 | McBride ..................... 116/206 |
| 4,971,196 A | * | 11/1990 | Kitamura et al. ........... 206/204 |
| 5,112,768 A | | 5/1992 | Carver |
| 5,180,598 A | | 1/1993 | Josefowicz |
| 5,224,373 A | | 7/1993 | Williams et al. |
| 5,293,996 A | * | 3/1994 | Duncan .................. 206/459.1 |
| 5,318,181 A | * | 6/1994 | Stover et al. ............ 206/459.1 |
| 5,439,648 A | | 8/1995 | Balderson et al. |
| 5,555,223 A | * | 9/1996 | Barainsky .................. 116/206 |
| 5,630,372 A | * | 5/1997 | Ramsey et al. ............. 116/206 |
| 5,644,899 A | * | 7/1997 | Truesdale .................... 53/447 |
| 5,658,819 A | * | 8/1997 | Hunphrey et al. .......... 438/600 |
| 5,756,356 A | * | 5/1998 | Yanagi et al. .............. 116/206 |
| 5,791,485 A | * | 8/1998 | Carbonneau ............... 206/720 |
| 5,797,344 A | * | 8/1998 | Ramsey et al. ............. 116/206 |
| 5,875,892 A | * | 3/1999 | Martin et al. ........... 206/459.1 |
| 5,882,994 A | * | 3/1999 | Araki et al. ................ 438/593 |
| 5,970,373 A | * | 10/1999 | Allen ......................... 438/624 |
| 6,103,351 A | * | 8/2000 | Ram et al. .................. 428/195 |
| 6,435,128 B2 | * | 8/2002 | Qiu et al. ................... 116/207 |

* cited by examiner

*Primary Examiner*—Diego Gutierrez
*Assistant Examiner*—R. Alexander Smith

(57) ABSTRACT

Exposure time is determined by a device which is sensitive to an environmental substance in a controlled environment. Embodiments include a humidity sensitive timer treated with a cobalt salt which changes colors after a certain exposure time within the controlled environment. Elapsed time is measured by exposing the timer to a humidity controlled environment and monitoring the timer for a change in color.

14 Claims, 1 Drawing Sheet

ELAPSED TIME INDICATOR FOR CONTROLLED ENVIRONMENTS AND METHOD OF USE

TECHNICAL FIELD

The present invention relates to a device and method of monitoring elapsed time in a controlled environment. The present invention has particular applicability in monitoring the elapsed time of an object in a controlled environment, such as an object in a semiconductor fabrication clean room.

BACKGROUND ART

During conventional semiconductor manufacturing, a batch or lot of semiconductor wafers undergo a multitude of processing steps including cleaning, coating, etching and testing. Carriers such as cassettes, boxes or boats are used to store, transport and transfer semiconductor wafers or a batch thereof from one processing step to another. Carriers are designed for the purpose of supporting the manufacturing and processing machinery which may either process the wafer while within the carrier or may permit removal for a particular operation and return of the wafers after a process operation.

Extreme demands placed on device features requires that the environment for housing the device fabrication process be stringently controlled for temperature, humidity, and environmental contaminants such as air borne chemicals or particles which may transferred to and damage individual or a batch of wafers. The potential sources of contamination include personnel, processing equipment, treatment chemicals, moving air and handling containers. The contaminants and particles are called defects which reduce semiconductor device yields.

The carriers themselves are also subject to contaminants and the fabrication process and are periodically cleaned to remove particles and/or chemical contaminants Because of the close and constant proximity of the wafers to the carriers, it is imperative that the carriers are maintained free of damaging contaminants. Due to the nature of these contaminants however, mere visual inspection of the carriers is inadequate and proper maintenance requires estimating the length of time that a carrier has been circulating within the processing operation.

Because of contamination concerns and the necessity of minimizing process variation, semiconductor wafers are tracked through many process steps to maintain a high level of control over the complete manufacturing process. Conventionally, semiconductor wafers have been tracked by a variety of systems including, for example: manual entries, such as by generating manual records; semi-automated systems, such as by a keyboard or bar code entry at various processing stations; or by automated systems through the use of elaborate radio frequency generators and transponder tags. Although tracking systems have been developed for the overall semiconductor device fabrication and for the tracking of a batch of wafers, there exists a need for a convenient method of tracking the time intervals among steps of critical operations within the overall process.

Carriers play a critical role in the manufacturing process, although the length of exposure time during the fabrication process and consequently their probability of contamination have not been the subject of adequate tracking, if at all. The exposure time is particularly difficult to estimate, since some operations require that wafers from one carrier be transferred to another carrier. Thus the carriers, as well as other equipment used during the manufacture of semiconductor devices, are independent of wafer tracking systems.

A variety of devices have been used to indicate exposure of an article to a certain level of contamination. Typically, the focus has been placed on identifying the amount or type of an alien gas or the relative humidity contained in an enclosed environment. Generally, these devices employ an indicating detector to signal that the surrounding environment, has reached unsuitable condition due to the presence or specified the contaminants. In addition, these devices are used to absorb the offending contaminant such as the absorption of moisture with an indicating desiccant. There are five main types of desiccants currently on the market: molecular sieves, activated alumnia, activated carbon, silica gel and clay. Although indicating devices have been known for signaling and absorbing specified contaminants in an enclosed environment, there has been no recognition that in a controlled environment, where the temperature, humidity and gas composition remain constant, a contamination indicating device may be employed as a timer.

Several simple and inexpensive contamination recording devices are known. For example, U.S. Pat. Nos. 5,224,373 and 4,098,120 describe the use of indicators for monitoring the relative humidity level of an enclosed container. The humidity indicators disclosed in these patents employ salts that change color upon exposure to certain levels of relative humidity, thereby permitting a visual indication of the level of humidity in the atmosphere of containers. Other humidity indicators have also been developed which employ a composition including an acidified aldehyde as, for example, an bacidified vanillin. U.S. Pat. No. 5,112,768 discloses methods and a device for sensing moisture by exposing a vanillin coated device to a test atmosphere. Humidity in the atmosphere chemically reacts with the coating to change its color, thereby indicating a level of moisture in the atmosphere.

Other examples of devices useful for detecting environmental conditions include the detection of an alien gas by a gas sensor. U.S. Pat. No. 5,439,648, for example, discloses a gas indicator to detect for the amount of carbon dioxide within the atmosphere of a food package thereby indicating the condition of the food product contain therein. The indicator provides an immediate warning by changing colors if the atmosphere inside the package changes to an unsuitable composition. The indicator is formed by utilizing a carbon dioxide sensitive ink printed as a set of strips on the sensor. Individual strips will change color depending on the amount of carbon dioxide in the package.

Although methods for detecting gases and humidity within an environment have been known as environmental condition monitors, the use of indicators in a controlled environment, such as a semiconductor clean room, is considered superfluous in that the environment does not greatly vary in composition or temperature. The use of indicators in a controlled environment as timers, however, has not been recognized.

Due to the precision and control required in semiconductor manufacturing, a need exists for improved monitoring of time interval between critical manufacturing operations. There is also a need to conveniently track the exposure time that a contaminant-sensitive object has been subjected to a controlled environment to accurately determine a cleaning or decontamination time for the object.

SUMMARY OF THE INVENTION

An advantage of the present invention is a device for measuring an elapsed time in a controlled environment. The device offers the advantage of conveniently and inexpensively tracking the length of time that an object has been exposed to the controlled environment.

Another advantage of the present invention is a method for monitoring elapsed time in a controlled environment. The method provides a simple means to monitor the length of time between processing steps.

Additional advantages and other features of the invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other advantages are achieved in part by a timer comprising a substrate and a substance-sensitive material on the substrate. It is advantageous for the substance-sensitive material to have a color which varies in accordance with exposure to a substance in the controlled environment thereby permitting convenient visual indicia of elapsed exposure time. A permeable transparent layer substantially covering the substance-sensitive material is further provided to prevent contamination of the controlled environment by the timer.

Another aspect of the present invention is a method of measuring elapsed time in a controlled environment. The method comprises: exposing a timer having a first readable exposure level to the controlled environment; and monitoring the timer for a second readable exposure level.

Additional advantages of the present invention will become readily apparent to those having ordinary skill in the art from the following detailed description, wherein the embodiments of the present invention are described, simply by way of illustration of the best mode contemplated for carrying out the present invention. As will be realized, the invention is capable of other and different embodiments, and its several details are capable of modification s in various obvious respects, all without departing from the present invention. Accordingly, the drawings and description are to be regarded as illustrative in nature, and not as restrictive.

BRIEF DESCRIPTION OF THE DRAWINGS

The various features and advantages of the present invention will become more apparent as a detailed description of the embodiments thereof is given with reference to the appended figure described below.

DESCRIPTION OF THE INVENTION

The present invention addresses and solves the problem of determining the length of time that an object has been exposed to an environment where the atmospheric composition is controlled and does not vary. In such a controlled environment, there are homogeneous substances in the atmosphere that remain fixed in amount. The rate of interaction between these substances, either by absorption or chemical reaction, and a substance-specific indicator can also be fixed. Consequently, the only variable which influences the complete absorption or reaction between the environmental substance and the indicator is the length of time that the indicator has been exposed to the substance in the controlled atmosphere. Elapsed time is determined by monitoring the substance-specific indicator for an indication or signal that a certain saturating amount of the substance has interacted with the indicator. Substance-specific indicators, thus, function as timers when employed in a controlled environment.

Figure 1:
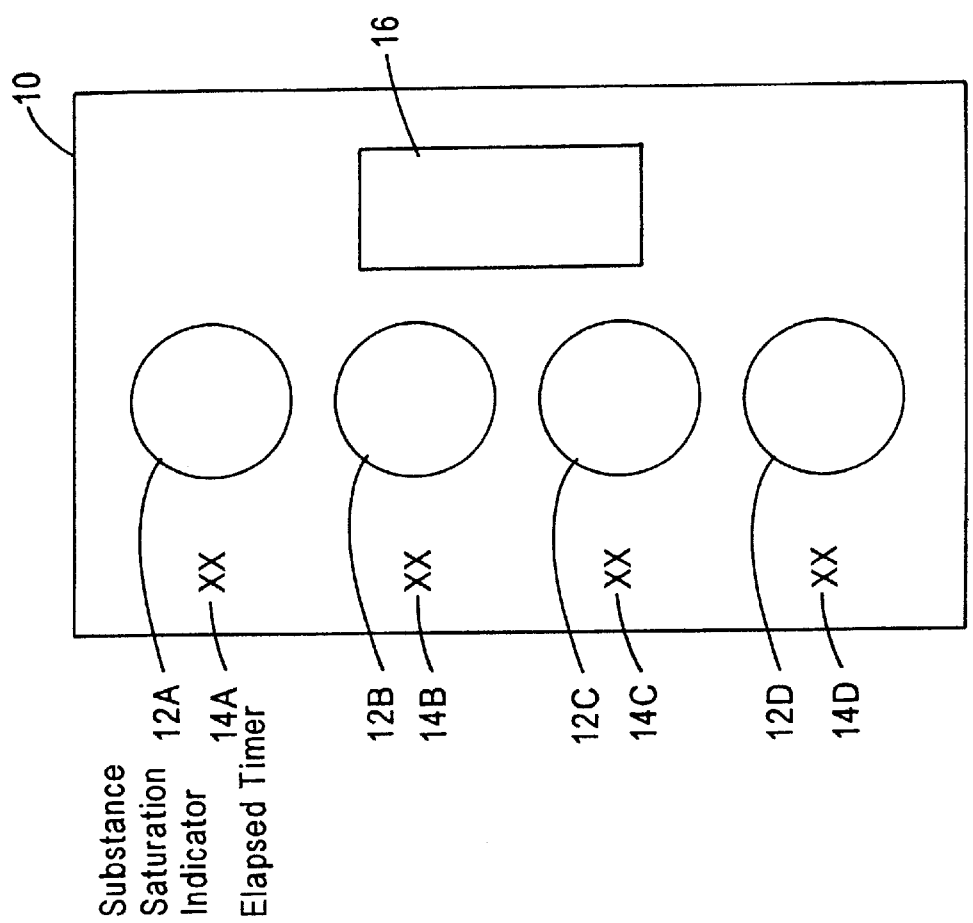
FIG. 1 schematically illustrates a timer of the present invention.

In accordance with the present invention, a timer comprises a substrate and a substance sensitive material on the substrate. The substance-sensitive material is provided which has a color that varies in accordance with exposure to a specific substance in the environment to which the timer is exposed. Additionally, an absorptive media can be impregnated with the substance-sensitive material and placed on the substrate to increase the performance of the timer. In an embodiment of the present invention, FIG. 1 illustrates a timer having substrate 10, a plurality of discrete patches of the substance-sensitive material thereon, numbered 12A through 12D, numerical indicia 14A through 14B near the discrete patches to represent predetermined time intervals, and a control patch 16.

Substrate 10 can be made of any material suitable for holding the substance-sensitive material. The substance-sensitive material, arranged in patches 12A–12D, each have a first readable color which changes to at least a second readable color upon saturation by the substance in the controlled environment. Each patch can be tailored to reach saturation at different exposure times, as for example by using differing amounts of the substance-sensitive material or each patch can have a different quantity of an absorptive media impregnated with the substance-sensitive material, thereby permitting different exposure time intervals among the patches. The numerical indicia, 14A–14D, represent the different time intervals associated with each discrete patch, e.g., the numerical indicia can be a series of time intervals including seconds, minutes, hours, days, weeks or months. For comparing the color of the discrete patches 12A through 12D, control patch 16 is provided which is representative of the saturation color of the substance-sensitive material.

In an embodiment of the present invention, when the environmental substance to be measured is humidity, an absorptive media, such as clay or silica gel, can be impregnated with the substance-sensitive material, such as an inorganic salt or an organic compound, which display color changes upon absorption of humidity. Alternatively, the absorptive media and substance-sensitive material can be blotter paper impregnated with inorganic salts or organic compounds. Representative organic compounds or inorganic salts which are useful in humidity detectors are acidified vanillin, magnesium nitrate, sugar, cuprous chloride, sodium bromide, nickel nitrate, ferric nitrate, cobalt bromide, ammonium nitrate, sodium dichromate, ferrous chloride, ammonium dichromate, nickel chloride, strontium chloride and cuprous nitrate. Additionally, it may be desirable to use various water-soluble dyes with certain salts which do not have a strong visible color of their own. Thus, Neptune Blue, BRA dye, Rhodamine B dye and Alphazurine 2 G Blue dye are useful in combination with some of the salts listed above. Other useful dyes and humidity indicating compounds have been disclosed in U.S. Pat. Nos. 5,224,373; 5,112,768; and 4,098,120, the disclosures of which are herein incorporated in their entirety by reference.

In an embodiment of the present invention, the substance-sensitive material is formed of a sheet of moisture absorbent blotter paper treated with a chemical solution of cobalt chloride. The cobalt salt will change color from a first readable blue color through a lavender color to a second readable pink color upon exposure to water vapor. The blue color is representative of a dry condition and the pink color is representative of a saturated state. A pink colored cobalt chloride salt can be regenerated by driving off the absorbed moisture thereby causing the salt to revert back to the first readable blue color and resetting the timer. A sheet of the impregnated blotter paper can be provided for each discrete patch 12A through 12D such that each of the patches have blotter paper with a different amount cobalt chloride and/or additives which will change color at different exposure times, thus providing a timer with a series of readable exposure levels signaling discrete time intervals.

Figure 2:
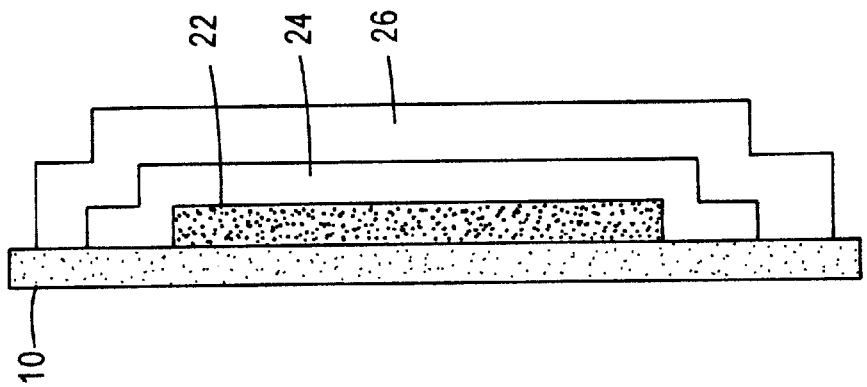
FIG. 2 is a cross-sectional view of a timer of the present invention.

In an embodiment of the present invention, as illustrated in FIG. 2, the timer can comprise a laminated structure, where substrate 10 supports substance-sensitive material 22 and a first layer, layer 24, can be laminated to substrate 10 substantially covering substance-sensitive material 22. Layer 24 should be of a material that is transparent to permit visual observations of changes in color and should be sufficiently permeable to allow communication between the environmental substance and substance-sensitive material 22.

In an embodiment of the present invention, layer 24 can be made of a flash spun, film sheet of high density polyethylene, such as Tyvek (E.I. DuPont de Nemours & Co.) such as manufactured by Richmond Technology, Inc. of Redlands Calif. Another commercially available material suitable for layer 24 is Marvelguard ECIA manufactured by Ludlow Corporation of Homer, La. In an embodiment of the present invention, layer 24 can be punctured with pin-sized holes substantially throughout the layer in order to shorten the time interval between readable exposure levels. Layer 24 can have holes having a diameter of about 0.01 mm to about 1 mm.

Optionally, the timer can further comprise a second layer, layer 26, laminated to the substrate or the first layer, such that it substantially covers the substance-sensitive material. Second layer 26, if present, is a transparent film which allows visual observations of color changes and is used to prevent interaction with of the substance-sensitive material and the environmental substance prior to the desired elapsed time determination. As with layer 24, layer 26 can be punctured with holes therein at the start of the elapsed time determination or layer 26 can be removed such that underlayer 24 is exposed.

According to the present invention, the timers are placed in a controlled environment and exposed therein or thereto. A controlled environment is an environment which has a substantially fixed amount of a substance such that the rate of interaction between the substance and the timer is constant. For example, in the manufacture of semiconductor devices, fabrication rooms (also refered to as clean rooms) are typically maintained to have a relative humidity which does not vary by more than about 5%, e.g., the environment can be maintained to within about 0.1% relative humidity. The temperature is also maintained and remains constant. Typically, the temperature does not vary by more than about 5° C., e.g. the temperature does not change by more than about 0.1° C.

When a timer, which is sensitive to humidity, is exposed to a clean room, saturation of the timer to humidity correlates to the length of time that the indicating timer has been exposed to the clean room environment. However, since there can be variations in the substance-sensitive material comprising the timer and variations between particular controlled environments, the timer should be initially calibrated before accurate exposure time intervals can be calculated. A method of calibrating the timer comprises initially exposing a timer having a first readable exposure level to a controlled environment at a first time and recording the first time. The timer can be exposed by punching several pin holes through a protective layer or by removing a protective layer thereon. The first time should be recorded as soon as the timer is exposed to the controlled environment. The first readable exposure level can be, for example, a blue color as when a cobalt chloride salt is used as the substance-sensitive material and the cobalt salt is dry. The timer is then monitored for a second readable exposure level as, for example, when the saturated cobalt salt turns to the color pink. Upon observing the second readable exposure level, a second time is recorded. Calibration of the timer is then determined by the difference between the first recorded time and the second recorded time, thereby giving a time interval for the length of time that it takes for a given amount of cobalt chloride to change from the color blue to the color pink in a humidity and temperature controlled environment. A control patch can be shaded the same color of pink as that of a saturated cobalt chloride to aid in the determination of complete saturation during monitoring of the timer. The above method can be repeated for different amounts of cobalt chloride thereby providing a timer which can have a plurality of discrete amounts of substance-sensitive material thereon which will change color at different exposure times.

After calibration, the timer can be used to measure the length of time that it or an object has been exposed to a controlled environment. In accordance with the present invention, a method of measuring elapsed time in a controlled environment comprises exposing a calibrated timer having a first readable exposure level to the controlled environment. As discussed above, the timer can be exposed by punching several pin holes through a protective layer or by removing a protective layer thereon. After exposing the timer to the controlled environment, the timer is simply monitored for a signal or indication, e.g. a second readable exposure level, that it has completely interacted with the environmental substance to which it is sensitive. The elapsed time indicator of the present invention can have an exposure time of up to about 90 days.

In an embodiment of the present invention, a calibrated timer having a first readable exposure level is placed in or on an object in a semiconductor clean room. The object can be a carrier, such as a cassette or boat for transporting semiconductor wafers or substrates, or a box which holds the cassette or boat. The calibrated timer is then exposed to the clean room environment and monitored for a second readable exposure level, a third readable exposure level, a forth readable exposure level or as many as desired for tracking discrete time intervals that the object has been exposed to the clean room environment. By placing a timer of the present invention on a cassette immediately after cleaning, individual cassettes can be tracked for the length of time that they have been in operation during the fabrication process. Moreover, a cleaning cycle can be established such that after a period of exposure time, expired cassettes are periodically subjected to a decontamination process. It should be noted that the timers of the present invention may not function properly if exposed to the decontamination procedure and are either removed or shielded prior to decontamination of the object.

A wafer carrier which is employed to transport semiconductor wafers should be cleaned to prevent contaminants from building up on its surface. The number of processing operations that a cassette or boat has been subjected to, and consequently used and handled, is directly proportional to the need for cleaning the carrier. It is believed that wafer carriers should be cleaned after about 40 operations, which is approximately equivalent to about 6 or 7 days for a carrier subjected to an uninterrupted flow from one process operation to the next. A quick scan of several carriers having timers of the present invention provides an immediate indication of which carriers are in need of decontamination and which carriers can be used for further operations.

As discussed, manufacturing of semiconductor devices requires a multitude of time critical steps, such as between a stripping or etching step and a post treatment rinsing or washing step. Due to the corrosiveness of the stripping and etching chemicals or process, a delay in post treatment could cause irreparable damage to the semiconductor wafer. Often, after completion of one step, a batch of wafers are placed in a queue awaiting the next processing step. To further ensure prompt attention to time critical steps, timers of the present invention can be used to indicate the length of time that has expired between steps. In an embodiment of the present invention, a calibrated timer can be placed on a cassette box holding a batch of wafers in a clean room subject to an etching or stripping step. Immediately after etching or stripping the wafers, the calibrated timer is exposed to the clean room environment. After the critical time has expired, the calibrated timer changes color indicating that the etched or stripped wafers must be processed immediately. The timers of the present invention can be calibrated to change colors at about 5 minutes to about 2 hours for a time critical process step. Monitoring the timer provides a simple visual indication of the elapsed time between critical steps and provides an easily identifiable alarm signaling the need for immediate action.

The present invention advantageously facilitates manufacturing deep-submicron memory devices, such as sub 0.1 micron devices, by minimizing process variation in a simplified manner with improved manufacturing throughput and reliability. The present invention is applicable to the manufacturing of various types of semiconductor devices, particularly semiconductor devices having a design rule of less than about 0.18 micron.

In the previous description, numerous specific details are set forth, such as specific materials, structures, chemicals, processes, and the like, to provide a better understanding of the present invention. However, the present invention can be practiced without resorting to the details specifically set forth. In other instances, well-known processing structures have not been described in detail to avoid unnecessarily obscuring the present invention.

Only the preferred embodiment of the invention and but a few examples of its versatility are shown and described in the present disclosure. It is to be understood that the invention is capable of use in various other combinations and environments and is capable of changes and modifications within the scope of the inventive concept as expressed herein.

What is claimed is:

1. A method of measuring elapsed time in a controlled environment, said method comprises:

exposing a calibrated timer having a first color to a temperature and humidity controlled environment; and monitoring the calibrated timer for a second color that is different from the first color, wherein the occurrence of the second color represents a predetermined length of time that the calibrated timer has been in the controlled environment, wherein the calibrated timer includes a humidity sensitive material that varies as a function of a duration to which the calibrated timer is exposed to the controlled environment, the controlled environment is a clean room and wherein the temperature does not vary by more than about 5° C. and the humidity does not vary by more than about 5%.

2. The method of claim 1, comprising placing the calibrated timer on an object and exposing the calibrated timer and object to the controlled environment.

3. The method of claim 2, comprising monitoring the calibrated timer for a third color that is different from the first color, wherein the occurrence of the third color represents a second predetermined length of time that the calibrated timer has been in the controlled environment.

4. The method of claim 2, comprising maintaining the temperature to vary by no more than about 0.1 in the controlled environment.

5. The method of claim 2, comprising maintaining the humidity to vary by no more than about 0.1% in the controlled environment.

6. The method of claim 2, comprising exposing the calibrated timer and object simultaneously to the controlled environment.

7. The method of claim 2, comprising cleaning the object after the occurrence of the second color.

8. The method of claim 2, wherein the calibrated timer comprises an absorptive media impregnated with an inorganic salt which displays color changes upon absorption of humidity.

9. The method of claim 1, comprising maintaining the temperature to vary by no more than about 0.1° C. and the humidity to vary by no more than about 0.1% in the controlled environment.

10. The method of claim 1, comprising placing the calibrated timer on a carrier containing semiconductor wafers and exposing the calibrated timer and carrier containing the semiconductor wafers to the controlled environment.

11. The method of claim 10, comprising maintaining the temperature to vary by no more than about 0.1° C. and the humidity to vary by no more than about 0.1% in the controlled environment.

12. The method of claim 10, comprising monitoring the calibrated timer to determine an exposure of about 6 or 7 days and then cleaning the carrier.

13. The method of claim 10, further comprising the steps of:

washing the carrier prior to the step placing the calibrated timer on the carrier, and prompting a subsequent washing of the carrier upon the occurrence of the second color.

14. The method of claim 1, wherein the calibrated timer is continuously exposed to the controlled environment prior to the occurrence of the second color.

* * * * *

UNITED STATES PATENT AND TRADEMARK OFFICE
CERTIFICATE OF CORRECTION

PATENT NO.    : 6,536,370 B2                                            Page 1 of 1
DATED         : March 25, 2003
INVENTOR(S)   : Eric Paton et al.

It is certified that error appears in the above-identified patent and that said Letters Patent is hereby corrected as shown below:

<u>Column 8,</u>
Line 20, after "0.1", insert -- ºC. --.

Signed and Sealed this

Sixth Day of May, 2003

JAMES E. ROGAN
*Director of the United States Patent and Trademark Office*